United States Patent [19]

Thompson et al.

[11] Patent Number: 5,425,954

[45] Date of Patent: Jun. 20, 1995

[54] TOPICAL AMINO ACID - VITAMIN COMPLEX COMPOSITIONS FOR PHARMACEUTICAL AND COSMETIC USE

[75] Inventors: Margaret A. Thompson, Walnutport, Pa.; Allan R. Cameron, Soldiers Point, Australia; John W. Manning, Decatur, Ga.

[73] Assignee: Curafas Incorporated, Walnutport, Pa.

[21] Appl. No.: 129,407

[22] Filed: Sep. 30, 1993

[51] Int. Cl.⁶ ............................................. A61K 7/48
[52] U.S. Cl. ................................. 424/401; 514/861; 514/863; 514/864
[58] Field of Search ............... 424/401; 514/861, 863, 514/864

[56] References Cited

U.S. PATENT DOCUMENTS

| | | | |
|---|---|---|---|
| 3,778,502 | 12/1973 | Aubin et al. | 514/400 |
| 3,849,576 | 11/1974 | Kalopissis | 514/649 |
| 3,997,659 | 12/1976 | Knohl et al. | 424/62 |
| 3,998,761 | 12/1976 | Gary et al. | 252/544 |
| 4,201,235 | 5/1980 | Ciavatta | 132/202 |
| 4,707,354 | 11/1987 | Garlen et al. | 424/47 |
| 4,732,892 | 3/1988 | Sarpotdar et al. | 514/178 |
| 4,743,442 | 5/1988 | Raaf et al. | 424/47 |
| 4,760,051 | 7/1988 | Pickart | 514/6 |
| 4,772,591 | 9/1988 | Meisner | 514/62 |
| 4,859,653 | 8/1989 | Morelle et al. | 514/2 |
| 4,963,591 | 10/1990 | Fourman et al. | 424/63 |
| 5,008,100 | 4/1991 | Zecchino et al. | 424/59 |
| 5,047,249 | 9/1991 | Rothman et al. | 424/543 |
| 5,133,958 | 7/1992 | Stuckler | 424/61 |
| 5,134,119 | 7/1992 | John et al. | 514/8 |
| 5,135,913 | 8/1992 | Pickart | 514/16 |
| 5,177,061 | 1/1993 | Pickart | 514/18 |
| 5,266,318 | 11/1993 | Taylor-McCord | 424/195.1 |

FOREIGN PATENT DOCUMENTS

| | | |
|---|---|---|
| 828729 | 12/1969 | Canada . |
| 0070048 | 1/1983 | European Pat. Off. . |
| 857243 | 12/1960 | United Kingdom . |
| WO92/00720 | 1/1992 | WIPO . |

*Primary Examiner*—Melvyn I. Marquis
*Assistant Examiner*—Robert H. Harrison
*Attorney, Agent, or Firm*—Howson and Howson

[57] ABSTRACT

The invention provides a composition for topical application to the skin comprising a mixture of Panthenol ($B_5$), Cod Liver Oil, Alpha Tocopherol Acetate, Arginine, Isoleucine, Leucine, Methionine, Phenylalanine, Threonine, and Valine in admixture with a suitable carrier. These compositions are particularly useful for the treatment of burns, cuts, abrasions, insect bites, inflammation from sun and wind exposure, dry skin, psoriasis, seborrheic dermatitis, and eczema.

2 Claims, No Drawings

TOPICAL AMINO ACID - VITAMIN COMPLEX COMPOSITIONS FOR PHARMACEUTICAL AND COSMETIC USE

FIELD OF THE INVENTION

The present invention relates generally to topically applicable pharmaceutical and cosmetic compositions, and more particularly, to compositions containing specific mixtures of amino acids and vitamins.

BACKGROUND OF THE INVENTION

The stratum corneum or horny layer of the epidermis of the human skin contains certain water soluble cellular components which protect internal tissues from external forces. These cellular components are composed of, among other things, small polypeptides and amino acids, and permit the stratum corneum to absorb and retain water, thereby preventing dryness of the skin.

Several morphological changes, including a decreased moisture content of the stratum corneum, coupled with reduced eccrine and sebaceous gland output can decrease the presence of these components which protect the skin and allow for loss of collagen, the major skin protein. These morphological changes which result in a loss of integrity of the horny layer of the skin can be caused by a variety of conditions. Among such conditions are environmental, e.g. sun or wind exposure, trauma or wounds, e.g. cuts, burns or abrasions, exposure to chemicals such as alkaline soaps, detergents, liquid solvents, oils, preservatives, and disease, eg. eczema, psoriasis, seborrheic dermatitis.

A wound is tissue loss or damage anywhere in the body caused by physical or chemical means, chronic irritation and/or inflammation of body tissue. Agents known to be useful in wound repair include anti-inflammatory agents and locally applied agents useful in the production of collagen and fibrous tissue.

Psoriasis is a skin disease characterized by thickened patches of inflamed skin, often red and/or marked by scales. This abnormality involves the production of skin cells about ten times faster than normal. However, the rate at which old cells are shed remains unchanged. The result is the accumulation of live cells in patches covered with dead, flaking skin. Presently known treatments for this condition involve local application of agents to reduce the inflammation and reduce the overproduction of skin cells.

Eczema is an inflammation of the skin often accompanied by scaling or blisters. It is a form of allergy which generates an exaggerated immune response. Seborrheic dermatitis is a form of eczema. Presently known treatments involve local application of agents capable of inhibiting the immune response and reducing inflammation.

It has been known for some time that the use of amino acids in combination, and the interaction of such amino acids with vitamins, has an ability to encourage the retention of water by the stratum corneum and the formation of a protective film upon the surface of the skin. [See, e.g., B. Idson, *Cosmetics and Toiletries*, 77–79 (1978); Johnson et al, *Cosmetics and Toiletries*, 83–84 (1973)]. Oral vitamin therapy can alleviate certain skin conditions, however, topical application of vitamin preparations can create higher local concentrations of vitamins to the affected areas of the skin. [See, e.g., T. Hindson, *Arch. Dermatol.*, 284–285 (1971)].

For example, compositions containing amino acids and vitamins have long been known to be used to treat skin conditions, including those affecting the hair, scalp, and nails. These compositions take the form of topical creams, shampoos, lotions and the like. Examples of such compositions are those described in Canadian Patent No. 828,729, U.S. Pat. Nos. 4,201,235, 5,133,958, International Patent Application Publication No. WO 92/00720, Great Britain Patent No. 857,243, U.S. Pat. Nos. 4,772,591, 3,849,576, European Patent Publication No. 70,048, U.S. Patent No. 5,135,913, 4,859,653 and 4,760,051. The compositions disclosed contain specific vitamins and amino acids either alone or in a variety of combinations. Although many prior art compositions have been described, their efficacy has been found to be inadequate. Consequently, in the treatment of a variety of skin conditions, particularly psoriasis, there is no prior art composition which has wide acceptance for a majority of individuals suffering with that condition.

There remains a need in the art, therefore, for topical compositions containing a specific combination of amino acids and ingredients which is efficacious in the treatment of a variety of skin conditions, e.g., wounds, environmentally caused inflammation, dry skin, psoriasis, seborrheic dermatitis, and eczema.

SUMMARY OF THE INVENTION

In one aspect, the present invention provides a novel composition which may be incorporated into topically applicable pharmaceutical formulations for the skin which-comprises a mixture of certain amino acids and vitamins. This mixture is surprisingly effective in the treatment of a variety of skin disorders, particularly psoriasis.

In a particular embodiment, a composition of this invention comprises Vitamin $B_5$ (Panthenol), Vitamins A and D in the form of Cod Liver Oil, Vitamin E (Alpha Tocopherol Acetate) in admixture with the amino acids Arginine, Isoleucine, Leucine, Methionine, Phenylalanine, Threonine and Valine. In another embodiment, the composition further contains Vitamin $B_6$, and the amino acids Glycine, Cysteine and Histidine. In an embodiment particularly useful for the treatment of psoriasis, the composition may contain coal tar. In an embodiment particularly useful for wound treatment, the composition may contain benzalkonium and allantoin.

In another aspect, the invention provides a pharmaceutical and/or cosmetic composition containing the formulation described above in admixture with a pharmaceutically acceptable base, and optionally containing other known agents including, but not limited to, bactericidal agents, water loss resistance barriers, viscosity agents, stabilizer agents, preservatives, and emulsifiers. Although it is possible to add dyes, perfumes, detergents or penetrating agents, in a preferred embodiment of the compositions of the invention, none of these compounds are present. The compositions, according to this invention, may be presented in different embodiments, including but not limited to creams, lotions, shampoos, and similar formulations.

In a further aspect of this invention, a method is provided for preparing the novel amino acid/vitamin compositions described herein and incorporating the same into topically applicable pharmaceutical compositions.

In yet a further aspect, this invention provides a process for treating the skin to eliminate or reduce the symptoms of a skin disorder as above described comprising applying directly to the surface of the skin a pharmaceutical composition described above.

Other aspects and advantages of the present invention will become apparent from the following detailed description thereof.

DETAILED DESCRIPTION OF THE INVENTION

The present invention provides novel compositions comprised of selected mixtures of amino acids and vitamins, which compositions are surprisingly effective in their ability to reduce inflammation and promote normal, healthy skin growth when applied to a variety of skin disorders. The topical application of these compositions to the skin acts to treat burns, cuts, abrasions, insect bites, inflammation from sun and wind exposure, dry skin, psoriasis, seborrheic dermatitis, and eczema. Other skin disorders and diseases which may be susceptible to treatment include, without limitation, Herpes Simplex I (cold sores), various forms of contact and allergic dermatitis, and mouth ulcers. In addition, it is believed that topical application of these compositions to animals may treat a variety of conditions including eczema.

The term "topical" as employed in this application relates to the introduction of formulations of the invention, incorporated in a suitable base or vehicle, at the site of the area for the exertion of local action. Accordingly, such topical compositions include those forms in which the formulation is applied externally by direct contact with the skin surface to be treated. Conventional forms for this purpose include but are not limited to creams, ointments, lotions, gels, pastes, powders and the like. The term "ointments" embraces formulations (including creams) having oleaginous absorption, water-soluble, and emulsion-type bases as described in *Remington's Practice of Pharmacy*, 11th Edition, 336 (1956).

A novel composition of the present invention is comprised of the following essential amino acids and vitamins, which, in specific combinations, provide a surprising result in enhancing the healing of the skin. Each of the components, herein described, is believed to contribute to the surprising efficacy of the composition by providing essential nutrients to the afflicted areas to support and complement the natural healing process of the human skin. The essential components of a composition of this invention are Vitamin $B_5$ (Panthenol), Vitamins A and D in the form of Cod Liver Oil, Vitamin E (Alpha Tocopherol Acetate) in admixture with the amino acids Arginine, Isoleucine, Leucine, Methionine, Phenylalanine, Threonine and Valine. Vitamin $B_6$ can be optionally added to the composition. Similarly, optional amino acids for addition to the composition include Glycine, Cysteine and Histidine.

More particularly, a preferred composition of the present invention can contain the mixture of amino acids and vitamins in the following proportions given in grams per 1000 grams of the composition and reported in Table I.

TABLE I

|  | Minimum | Maximum |
| --- | --- | --- |
| Panthenol ($B_5$) | 2.5 | 10.0 |
| Cod Liver Oil (Vitamins A & D) | 2.5 | 10.0 |
| Alpha Tocopherol Acetate (Vitamin E) | 1.75 | 7.0 |
| Vitamin $B_6$ (Optional) | 2.5 | 10.0 |

TABLE I-continued

|  | Minimum | Maximum |
| --- | --- | --- |
| Arginine | 0.6 | 2.4 |
| Isoleucine | 0.6 | 2.4 |
| Leucine | 0.6 | 2.4 |
| Methionine | 1.4 | 5.6 |
| Phenylalanine | 0.6 | 2.4 |
| Threonine | 0.6 | 2.4 |
| Valine | 0.6 | 2.4 |
| Glycine (Optional) | 0.6 | 2.4 |
| Cysteine (Optional) | 0.6 | 2.4 |
| Histidine (Optional) | 0.6 | 2.4 |

A composition of the formulation of Table I may be used cosmetically to treat skin irritations. Alternatively, as described below, the compositions may be supplemented by active pharmaceutical ingredients, where desired, as well as conventional ingredients suitable for topical formulations. Optional antibacterial and antioxidant agents in the compositions can perform their ordinary functions in an enhanced manner due to the advantages provided by the basic composition. Two specific formulations based on this basic composition of Table I are described in detail in Examples 1 and 2.

While not wishing to be bound by theory, the inventors contemplate that the compositions work by approximating the water soluble cellular components of the skin as closely as possible and by providing the amino acid building blocks of the epidermal proteins to prevent the loss of water and protein due to the above-described skin conditions. The following analysis of how the various components of the composition contribute to the overall effect is therefore theoretical.

Because of its required presence in the formation of epidermal proteins, the presence of arginine in the composition is believed to promote normal epidermal cell functions and is considered necessary for cell maturation in rapidly dividing systems such as observed in psoriasis. Arginine also stimulates the activity of synthetase in the urea cycle and participates in the synthesis of guanidinoacetic acid, polyamines, creatine, and collagen which are essential components of the epidermis. [See E. Braverman and C. Pfeiffer, *The Healing Nutrients Within*, 163–170 (1986)]. By lowering the level of polyamines through the reduction of pyrimidine synthesis, arginine reduces the levels of nucleic acid available for DNA formation. As DNA formation requires the presence of nucleic acids, reduced levels of nucleic acids may effectively retard the rapid cell division which is characteristic of psoriasis. [See Braverman and Pfeiffer, cited above; Devlin et al, *Textbook of Biochemistry with Clinical Correlations*, 12:491–510 (1992)]. Lastly, arginine is the primary substrate for blood vessel endothelial factor responsible at the local level for stabilizing blood flows and thus may aid in the repair and reoxygenation of damaged tissue.

Isoleucine, leucine, and valine are branched chain amino acids which are believed to function similarly in the present compositions, have regulatory effects on protein metabolism, and may be essential for both energy production and for use in stress or trauma. The side chains on these amino acids contain methyl groups which are used anabolicly both in ketogenic and glucogenic metabolic pathways of energy production. Energy production is required for the protein metabolism required during trauma or stress to the skin to replenish the proteinaceous components of the epidermis and dermis.

Methionine is theorized to serve three functions in the present invention. First, it acts as a sulphur and methyl donor and contributes these compounds to the synthesis of dermal proteins essential in cell repair and growth. Second, it lowers histamine levels. As part of the immune system, histamine is released by the body in response to cell injury and acts to increase blood flow to the capillaries of the injured region, and causes swelling, redness, and increases the permeability of the capillary walls. The presence of methionine reduces these effects. Lastly, methionine is an essential component of methionine enkephalin, one of the body's natural pain killers.

Phenylalanine is also a constituent of methionine enkephalin. In addition, phenylalanine is a component of cholecytokenin, another natural pain reliever. Phenylalanine also has the ability to block the degradation of endorphins and enkephalins, normally occurring pain killers.

Threonine acts as an immunity booster by increasing local concentrations of immunoglobulins. Immunoglobulins impede cancer-like growth which is comparable to that observed in patients suffering from psoriasis. [See Braverman and Pfeiffer, cited above, 229–236].

Additionally, glycine, cystine, and histidine may be optionally added to the formulation of the invention. Glycine acts as a nutrient and is especially desirable in the treatment of burns and skin trauma. Dimethyl glycine may also be used as it may be converted into glycine and, thus, stimulate the immune system. [See, e.g., Devlin, cited above, at pages 607–680].

Cysteine plays an essential role in energy metabolism as a structural component of several tissues and hormones. Cysteine also acts as an detoxifying agent and an antioxidant due to its ability to stimulate the production of glutathione—a powerful detoxifying agent and antioxidant. [See Braverman and Pfeiffer, cited above, at pages 85–119]. As such, cysteine is useful for a range of activities, including treatment of psoriasis.

Histidine promotes tissue growth and repair. Clinical studies have demonstrated the histidine is effective in treating psoriasis. [See, e.g., *Acta Derm Venereol.*, 67:274–275 (1987)].

Vitamin A is believed necessary for normal growth of most somatic cells, especially epithelial cells. Vitamin A deficiency causes atrophy of epithelial cells, proliferation of basal cells, and increased growth and differentiation of new cells into horny epithelium. This results in symptoms of dryness, scaling of the skin, and excessive keratinization. In addition, because damaged epithelial cells incur an increased risk of becoming infected, Vitamin A acts as an "anti-infection" agent due to its ability to repair cells and stimulate normal cell growth.

Vitamin D stimulates the production of a calcium binding protein, possibly calcium calmodulin, necessary for calcium absorption and metabolism. As normal cell growth is dependent on the absorption of calcium, Vitamin D is theorized to promote epithelial growth and healthy granulation and healing of damaged skin cells.

Vitamin E, used in this invention in the form of alpha tocopherol acetate, prevents the oxidation of fatty acids, key components of cellular membranes. In addition, vitamin E protects lipids and lipoproteins in cell membranes which allows cells to retain water binding capacity and prevents dry skin. Vitamin E also aids in the slowdown of peroxide formation and, in doing so, protects the body from damage by peroxide radicals, thus stabilizing cell membranes and promoting normal cell function. [See, e.g., *Cosmetics and Toiletries*, 93:pp-pp (1978)]. Vitamin E also enhances the immune system by suppressing prostaglandins, cellular components of the immune system which are sensitive to oxidation. [See Devlin, cited above, 1118–1145]. Panthenol (vitamin $B_5$) is a biologically active analog of pantothenic acid, a vitamin of the B-complex group and normal constituent of the skin and hair. When panthenol is applied to the skin topically, it is converted into pantothenic acid and is largely incorporated in coenzyme (CoA) which has several roles in cellular metabolism. Panthenol has a pro-vitamin and water-soluble character which combine to yield a non-irritating and non-sensitizing moisturizing agent. The humectant character of panthenol enables it to hold water in the product or attract water from the environment to yield moisturizing effects.

Lastly, the present invention may optionally include vitamin $B_6$ in the form of pyridoxal phosphate which functions as a coenzyme for many different chemical reactions relating to amino acid and protein metabolism, including the transamination process for the synthesis of amino acids. As a result, pyridoxal acid plays a key role the metabolism of essential structural proteinaceous components of the skin [Braverman and Pfeiffer, cited above, 17].

As described above, cod liver oil can serve as a source of vitamins A and D, panthenol as a source for vitamin $B_5$, and alpha tocopherol acetate as a source for vitamin E. Other conventional sources of these vitamins may also be employed in the formulations.

The basic composition as described above may be desirably employed without additional additives both as a treatment for dry skin or as a pharmaceutical application for a variety of skin disorders, i.e., psoriasis and the other conditions identified above.

Alternatively, the basic composition described above may be formulated into a pharmaceutical product for selected skin conditions, and may contain other conventional active ingredients. For example, in a composition particularly useful for the treatment of psoriasis, the composition may contain coal tar as an active ingredient. Similarly, in an embodiment particularly useful for wound treatment, the composition may contain as active ingredients allantoin or benzalkonium or other antiseptic, antibacterial components.

For the preparation of preferred embodiments of the present invention, Table II provides a list of desirable active ingredients in grams per 1000 grams of the composition serving particularly desirable functions, which may be admixed with the above described amino acid-vitamin formulations of the invention.

TABLE II

| Substance | Weight | Function |
| --- | --- | --- |
| Coal tar | 0.5–5.0 | antiseptic, antipruritic, keratoplastic |
| Allantoin | 0.5–2.0 | skin protectant, skin ulcer therapy, promote tissue growth |
| Benzalkonium chloride | 0.1–0.13 | antiseptic |
| Methyl salicylate | 10–60 | counter-irritant |
| Camphor | 0.1–3.0 | analgesic, anaesthetic, antipruritic |
| Menthol | 0.1–1.0 | analgesic, anaesthetic, antipruritic |
| Eucalyptus oil | 1.0–3.0 | counter-irritant, |

TABLE II-continued

| Substance | Weight | Function |
|---|---|---|
| antiseptic | | |

Compositions of the present invention may additionally contain conventional inert ingredients. By inert ingredients is meant conventional preservatives, water loss resistance barriers, viscosity stabilizers, preservatives, emulsifiers, detergents and other conventional components of topical formulations for human or animal skin which do not alter the effect of the basic composition. An exemplary, non-exclusive listing of conventional inert ingredients which may be admixed with the basic composition of amino acids and vitamins as described above is described in Table III below, with percentages by weight of the total composition, and with conventionally accepted functions indicated.

TABLE III

| Ingredient | Percent | Fraction |
|---|---|---|
| Water | 50.25%–50.35% | aqueous base |
| mineral oil | 15% | oil base |
| glycerin | 6.5% | moisture protecting agent |
| paraffin wax | 15% | stabilizer |
| cetyl stearyl alcohol | 6% | solvent |
| chlorobutanol | 0.5% | solvent |
| sodium dehydroacetate (SDA-40) alcohol | 1.5% | preservative |
| ceteth-20 | 1.5% | lubricant |
| methyl paraban | 0.25% | preservative |
| propyl paraban | 0.15% | preservative |
| diazolidinyl urea | 0.2% | preservative |
| sodium benzoate | 0.1% | preservative |
| ethylenediaminetatraacetic acid (FMTA) | 0.1% | enhancer, promotes delivery to the skin |

The basic compositions as well as the cosmetic or pharmaceutical compositions according to the invention may be prepared by conventional methods [See, e.g., *Remington's Practice of Pharmacy*, 11th Edition, 336 (1956)]. For example, the essential ingredients, i.e., the essential amino acids and vitamins, and any optional conventional active ingredients, may first be dissolved in a suitable quantity of a pharmaceutically acceptable base or carrier, e.g., water, oil or oil-in-water. That resulting solution may be emulsified an any suitable fatty base, which is inert with respect to the skin, in which the solution of active ingredients may be emulsified. This process is accomplished by mixing solutions of the various components at temperatures suitable to permit ready mixture without inactivation of the individual components, resulting in the formation of a stable homogenous composition. In this preparation, bactericidal agents, water loss resistance barriers, viscosity stabilizers, preservatives, and emulsifiers may be added. Although it is possible to add dyes, perfumes, detergents or penetrating agents, in a preferred embodiment of the compositions of the invention, none of these compounds are present. The resulting composition is preferably in the form of a stable emulsion. By "stable" is meant that the composition remains in a homogenous emulsified form for periods up to 90 days at temperatures up to 37° C. for about 2 years and at room temperature (approximately 23° C.). A preferred method of preparation is described in detail in Examples 1 and 2 below.

The compositions of the present invention may be employed in methods for treating the skin. More specifically, the compositions may be employed in a method for reducing the irritation of a skin disorder comprising administering directly onto the affected area of the skin of a mammal in need of such treatment, e.g., desirably a human, an effective amount of a composition according to this invention. According to these methods, effective amounts of the selected composition of the invention are topically applied to the surface of skin disorder. By "effective amount" is meant a quantity of the composition in its particular formulation, e.g., cream, lotion, etc., to lightly cover the affected area of skin. Because none of the components of the compositions of this invention in their appropriate percentages in the formulations can damage the skin, the appropriate dosage and application regimen can be determined by the individual applying the composition, considering various factors, including the type of skin disorder to be treated, extent and severity of outbreak, possible co-treatment with a systemically-acting medicament, and other factors. Applications of the compositions may therefore range from one to multiple applications daily for the duration of the eruption on the surface of the skin caused by the particular disorders. Use of the basic composition or any of the other defined compositions of this invention for the treatment of dry skin alone may be continuous.

The following Examples 3 through 5 below describe the uses of the compositions of this invention and illustrate several skin disorders which are successfully treated by the formulation of the invention. For most skin disorders, two applications of an effective amount daily yield noticeable improvement within four days. For more traumatized skin conditions, three to four applications per day is recommended. Generally, improvement is observed in both cases in approximately four days. Several factors have been observed to reduce the rate of healing, including smoking, age, psychological stress, use of oral contraceptives, poor nutrition, poor blood circulation to the affected area, infection, certain drugs, and the location of the skin disorder.

The compositions of the present invention, in addition to their use in treating the above-named skin disorders in humans, may also be useful in treating similar disorders in animals.

The following examples which demonstrate the compositions and methods of the invention are for illustrative purposes only and do not limit the scope of this invention. As demonstrated in the following examples, the compositions of this invention have produced surprisingly good results in a variety of skin disorders. Although it is not clear why the combination of components provided in this composition are so effective, it is clear from reports of the individuals discussed in the examples that the composition has advantages over prior art compositions designed for similar uses.

EXAMPLE 1

Preparation of a Topical Pharmaceutical Composition for the Treatment of Psoriasis, Eczema, and Dermatitis The following Table IV describes the phase in which each ingredient is incorporated into the composition of the invention and provides the amounts in grams per thousand grams of the formulation of each ingredient:

TABLE IV

| Phase | Ingredient | Amount |
| --- | --- | --- |
| 1 | water | 503.5 |
|   | glycerin | 65.0 |
|   | panthenol (vitamin B5) | 5.0 |
|   | methyl paraben | 2.5 |
|   | EDTA | 1.0 |
| 2 | mineral oil | 150.0 |
|   | paraffin wax | 150.0 |
|   | cetyl stearyl alcohol | 60.0 |
|   | ceteth-20 | 15.0 |
|   | chlorobutanol | 5.0 |
|   | cod liver oil (vitamins A and D) | 5.0 |
|   | tocopheryl acetate (vitamin E) | 3.5 |
|   | propyl paraben | 1.5 |
| 3 | diazolidinyl urea | 2.0 |
|   | sodium benzoate | 1.0 |
| 4 | SDA-40 alcohol | 15.0 |
|   | coal tar | 5.0 |
| 5 | methionine | 2.8 |
|   | arginine | 1.2 |
|   | leucine | 1.2 |
|   | isoleucine | 1.2 |
|   | phenylalanine | 1.2 |
|   | threonine | 1.2 |
|   | valine | 1.2 |

The composition is prepared as follows:

(a) In a mixing tank, phase 1 components are weighed and heated to 77° C.;

(b) In a separate tank, phase 2 components are weighed and heated to 80° C.;

(c) After cooling the material in the mixing tank to 75° C., phase 2 solution is added into the mixing tank with phase 1 and mixed until smooth, then cooled to 40° C.;

(d) At 40° C. premixed phase 3 is added to the mixing tank while mixed, then cooled to 35° C.;

(e) At 35° C. premixed phase 4 is added to the mixing tank while mixing until smooth, then cool to 30° C.;

(f) At 30° C. each ingredient of phase 5 is weighed and added into the mixing tank while mixing, then cooled to 25° C. A stable homogenous emulsion having a creamy consistency is thereby produced.

Example 2

Preparation of a Topical Pharmaceutical Composition for First Aid Treatment

The following Table V describes the phase in which each ingredient is incorporated into this composition of the invention and provides the amounts in grams per thousand grams of the formulation of each ingredient:

TABLE V

| Phase | Ingredient | Amount |
| --- | --- | --- |
| 1 | water | 502.5 |
|   | glycerin | 65.0 |
|   | panthenol (vitamin B5) | 5.0 |
|   | methyl paraben | 2.5 |
|   | EDTA | 1.0 |
| 2 | mineral oil | 150.0 |
|   | paraffin wax | 150.0 |
|   | cetyl stearyl alcohol | 60.0 |
|   | ceteth-20 | 15.0 |
|   | chlorobutanol | 5.0 |
|   | cod liver oil (vitamins A and D) | 5.0 |
|   | tocopheryl acetate (vitamin E) | 3.5 |
|   | propyl paraben | 1.5 |
| 3 | diazolidinyl urea | 2.0 |
|   | sodium benzoate | 1.0 |
| 4 | SDA-40 alcohol | 15.0 |
|   | benzalkonium | 1.0 |
|   | allantoin | 5.0 |
| 5 | methionine | 2.8 |
|   | arginine | 1.2 |
|   | leucine | 1.2 |
|   | isoleucine | 1.2 |
|   | phenylalanine | 1.2 |
|   | threonine | 1.2 |
|   | valine | 1.2 |

The composition is prepared as follows:

(a) In a mixing tank, phase 1 components are weighed and heated to 77° C.;

(b) In a separate tank, phase 2 components are weighed and heated to 80° C.;

(c) After cooling the material in the mixing tank to 75° C., phase 2 solution is added into the mixing tank with phase 1 and mixed until smooth, then cooled to 40° C.;

(d) At 40° C., premixed phase 3 is added to the mixing tank while mixed, then cooled to 35° C.;

(e) At 35° C., premixed phase 4 is added to the mixing tank while mixing until smooth, then cool to 30+ C.;

(f) At 30° C., each ingredient of phase 5 is weighed and added into the mixing tank while mixing, then cooled to 25° C. A stable homogenous emulsion having a creamy consistency is thereby produced.

Example 3

Use of the Invention to Treat Psoriasis/Eczema

A. A 64 year old man in good health suffering from psoriasis for several years applied a topical solution of the invention as described in Example 1 to his irritated skin surface 2 times a day for 30 days. Application of this solution resulted in a partial clearing of the irritated area in 4 days.

B. A woman, approximately 55 years old, suffering from psoriasis for 14 years applied a topical solution of the invention of Example 1 to her irritated skin surface 3 to 4 times a day for 7 days. Application of this solution resulted in a partial clearing of the irritated area in 7 days.

C. A 52 year old woman suffering from eczema on her legs and fingernails applied a topical solution of the invention as described in Example 2 to the area of skin trauma 2 times a day for 7 days. Application of this solution resulted in partial healing of the afflicted area in 2 days, and total healing in 7 days.

Example 4

Use of the Invention to Treat Cuts, Burns, and Abrasions

A 78 year old man suffering from a 1 inch deep cut on his finger applied a topical solution of the invention as described in Example 2 to the injured area 2 times a day for 2 weeks. Application of the solution resulted in partial healing in 2 weeks and complete healing in one month.

Example 5

Use of the Invention to Treat Cold Sores

A 28 year old man suffering from cold sores applied a topical solution of the invention of Example 2 to the affected area 1 to 3 times a day for 8 days. Application of this solution resulted in partial healing of the afflicted area in 8 days.

Numerous modifications of this invention are encompassed by the above description and the scope of the following claims. For example, other suitable optional ingredients may be employed in the composition of this invention which are obvious to one of skill in the art considering the present disclosure. Similarly other skin disorders other than those described in the examples may be treated with the compositions of this invention. It should be understood that various changes may be made in the process as herein described without significantly affecting the resultant formulations. Thus, various modifications in conditions as to time, temperature, and various changes in procedure differing from those herein given as illustrative of the preferred embodiments of the invention may be made without departure from the scope thereof.

What is claimed is:

1. A composition for treating psoriasis consisting essentially of a mixture of the following components in amounts expressed per gram of 1000 gm total composition:

| component | amount |
| --- | --- |
| water | 503.5 |
| glycerin | 65.0 |
| panthenol [(vitamin B$_5$)] | 5.0 |
| methyl paraben | 2.5 |
| EDTA | 1.0 |
| mineral oil | 150.0 |
| paraffin wax | 150.0 |
| cetyl stearyl alcohol | 60.0 |
| ceteth-20 | 15.0 |
| chlorobutanol | 5.0 |
| cod liver oil [(vitamins A and D)] | 5.0 |
| tocopherol acetate [(vitamin E)] | 3.5 |
| propyl paraben | 1.5 |
| diazolidinyl urea | 2.0 |
| sodium benzoate | 1.0 |
| SDA-40 alcohol | 15.0 |
| coal tar | 5.0 |
| methionine | 2.8 |
| arginine | 1.2 |
| leucine | 1.2 |
| isoleucine | 1.2 |
| phenylalanine | 1.2 |
| threonine | 1.2 |
| valine | 1.2 |

2. A composition for treating wounds consisting essentially of a mixture of the following components in amounts expressed per gram of 1000 gm total composition:

| component | amount |
| --- | --- |
| water | 502.5 |
| glycerin | 65.0 |
| panthenol [(vitamin B$_5$)] | 5.0 |
| methyl paraben | 2.5 |
| EDTA | 1.0 |
| mineral oil | 150.0 |
| paraffin wax | 150.0 |
| cetyl stearyl alcohol | 60.0 |
| ceteth-20 | 15.0 |
| chlorobutanol | 5.0 |
| cod liver oil [(vitamins A and D)] | 5.0 |
| tocopherol acetate [(vitamin E)] | 3.5 |
| propyl paraben | 1.5 |
| diazolidinyl urea | 2.0 |
| sodium benzoate | 1.0 |
| SDA-40 alcohol | 15.0 |
| benzalkonium chloride | 1.0 |
| allantoin | 5.0 |
| methionine | 2.8 |
| arginine | 1.2 |
| leucine | 1.2 |
| isoleucine | 1.2 |
| phenylalanine | 1.2 |
| threonine | 1.2 |
| valine | 1.2 |

* * * * *

UNITED STATES PATENT AND TRADEMARK OFFICE
CERTIFICATE OF CORRECTION

PATENT NO. : 5,425,954
DATED : June 20, 1995
INVENTOR(S) : Margaret A. Thompson, Allan R. Cameron, and John W. Manning It is certified that error appears in the above-indentified patent and that said Letters Patent is hereby corrected as shown below:

Tile page, item [57],

"Abstract" should read -- Abstract of the Disclosure --.

Col. 7, in Table III, line 36, "(FMTA)" should read -- (EDTA) --.

Col. 10, line 25, "30+" should read -- 30° --.

Col. 11, Claim 1, in the table, line 32, "[(vitamin $B_5$)]" should be deleted; line 40, "[(vitamins A and D)]" should be deleted; and line 42, "[(vitamin E)]" should be deleted.

Col. 12, Claim 2, in the table, line 22, "[(vitamin $B_5$)]" should be deleted; line 29, "[(vitamins A and D)]" should be deleted; and line 31, "[(vitamin E)]" should be deleted.

Signed and Sealed this

Twentieth Day of February, 1996

BRUCE LEHMAN

Attest:

Attesting Officer

Commissioner of Patents and Trademarks